United States Patent [19]
Kazi et al.

[11] Patent Number: 5,377,685
[45] Date of Patent: Jan. 3, 1995

[54] ULTRASOUND CATHETER WITH MECHANICALLY STEERABLE BEAM

[75] Inventors: Arif Kazi, Bensheim, Germany; Jeanne Rougeot; Lynn L. Li, both of Montreal, Canada; Louis D. Dufour, Longueuil, Canada

[73] Assignee: Baylis Medical COmpany, Inc., Quebec, Canada

[21] Appl. No.: 169,306

[22] Filed: Dec. 17, 1993

[51] Int. Cl.⁵ .................................. A61B 8/12
[52] U.S. Cl. .................. 128/662.06; 128/660.10
[58] Field of Search ............ 128/662.05, 662.06, 128/4, 6, 24 AA; 604/22

[56] References Cited

U.S. PATENT DOCUMENTS

| | | | |
|---|---|---|---|
| 4,576,177 | 3/1986 | Webster, Jr. | 128/660.03 |
| 4,794,931 | 1/1989 | Yock | 128/662.06 |
| 4,887,605 | 12/1989 | Angelsen et al. | 128/660.03 |
| 4,893,628 | 1/1990 | Angelsen | 128/660.03 |
| 4,899,757 | 2/1990 | Pope, Jr. et al. | 128/662.06 |
| 4,911,170 | 3/1990 | Thomas, III et al. | 128/662.06 |
| 4,917,097 | 4/1990 | Proudian et al. | 128/662.06 |
| 4,930,515 | 6/1990 | Terwilliger | 128/662.06 |
| 4,951,677 | 8/1990 | Crowley et al. | 128/662.06 |
| 5,000,185 | 3/1991 | Yock | 128/662.06 |
| 5,002,059 | 3/1991 | Crowley et al. | 128/662.06 |
| 5,048,529 | 9/1991 | Blumenthal | 128/662.06 |
| 5,109,859 | 5/1992 | Jenkins | 128/662.06 |
| 5,131,397 | 7/1992 | Crowley | 128/662.06 |
| 5,168,864 | 12/1992 | Shockey | 128/662.06 |
| 5,174,296 | 12/1992 | Watanabe et al. | 128/662.06 |
| 5,188,111 | 2/1993 | Yates et al. | 128/557 |

FOREIGN PATENT DOCUMENTS

2212267 7/1989 United Kingdom .

OTHER PUBLICATIONS

Transvascular Intracardiac Applications of a Miniaturized Phased-Array Ultrasonic Endoscope—by Lilliam M. Valdes-Cruz, MD, et al. Division of Pediatric Cardiology, 225 Dickinson Street, (H-814-A), San Diego, Ca. 92103-Circulation-vol. 83, No. 3, Mar. 1991, pp. 1023-1027.

*Primary Examiner*—Francis Jaworski
*Attorney, Agent, or Firm*—Galgano & Burke

[57] ABSTRACT

The catheter has a mechanically steerable beam which can be directed at a variable angle with respect to an axis of rotation of the catheter. The ultrasonic transducer can be mounted in a pivoting head and steered by shape memory alloy wires subject to controlled ohmic heating. A feedback system including a marker wire embedded in a capsule wall of the catheter's outer tube can be used to determine the beam angle.

16 Claims, 5 Drawing Sheets

ULTRASOUND CATHETER WITH MECHANICALLY STEERABLE BEAM

FIELD OF THE INVENTION

The present invention relates to an intravascular or intra-cardiac ultrasound catheter of the type which is rotated within a heart chamber, an artery or vein to produce an ultrasound image of the interior of the blood vessel or heart. The invention relates further to such a catheter which is able to produce an image at a desired position forward of the catheter tip by controlling the angle of the ultrasound beam with respect to its rotation axis through a range.

BACKGROUND OF THE INVENTION

Miniature ultrasound probes for imaging blood vessels are well known in the art (for example, see U.S. Pat. No. 4,576,177 to Webster, Jr.). In conventional imaging systems, the catheter has an outer tube containing a rotatable flexible shaft connected to an ultrasound transducer tip (see U.S. Pat. No. 4,794,931). By rotating the transducer tip, a two dimensional image slice of the blood vessel can be obtained. By linearly moving the ultrasound transducer inside the outer tube, or by moving the outer tube within the blood vessel, images of the blood vessel at various points can be obtained. The ability to image forward of the catheter tip at a controllable distance and angle in front of the tip has been either difficult or not possible.

In U.S. Pat. No. 5,174,296, an ultrasound probe is described which looks forward into a blood vessel with a pie segmented piezoelectric transducer facing forward with each segment at a different angle with respect to the rotation axis. While such a probe can produce images at different forward positions without requiring linear movement, and in a forward direction (this allows an arterial obstruction to be imaged before reaching it), the very small piezoelectric segments have limited imaging power, and therefore the ability to image clearly is reduced.

SUMMARY OF THE INVENTION

It is an object of the invention to provide an ultrasound catheter probe which is able to generate an image of a blood vessel inside section or the heart by rotation of the ultrasound beam about a lengthwise axis of the catheter and by adjusting an angle of the beam with respect to the lengthwise axis.

It is also an object of the invention to provide an intravascular ultrasound catheter probe which is able to generate an image of a blood vessel at a controllable point forward of the catheter tip. Similarly, it is an object of the invention to provide an intra-cardiac ultrasound catheter probe which is able to generate an image within the various chambers of the heart at a controllable point forward of the catheter tip.

It is a further object of the invention to provide an intravascular or intra-cardiac ultrasound catheter probe which is able to vary its beam angle to view a blood vessel wall or heart chamber at different angles resulting in different image characteristics.

According to the invention, there is provided an ultrasound catheter comprising an outer tube having a lumen, a sonolucent closed distal end and a proximal end, a rotatable drive shaft provided in the lumen, the shaft including an electric signal transmission cable, a tip member connected to the shaft and provided at the distal end, the tip member having a lengthwise axis of rotation when rotated by the shaft, an ultrasound transducer mounted in the tip member and connected to the cable for generating an ultrasound beam, and beam directing means for directing the ultrasound beam radially outward with respect to the lengthwise axis at a variable angle thereto and for controllably adjusting the angle. In this way, an ultrasonograph forward of the tip at a desired distance and angle can be obtained by rotation of the drive shaft and adjustment of the angle.

The beam angle can be controllably adjusted according to the invention by pivoting the transducer, reflecting the beam emitted by a fixed transducer off a pivoting planar mirror, or reflecting the beam emitted by a fixed transducer off a curved linearly translatable mirror. When the transducer is designed to pivot, it can be mounted in a ball-and-socket mount or a pivot/hinge mount. The beam directing means can be provided by one of a variety of actuator mechanisms to cause the pivoting or translation required to adjust the beam angle. Shape memory alloy wires electrically heated to controllably contract are one possibility for making a suitable actuator. The forward-reverse action of the actuation can be provided by a pair of actuators working in opposite directions or by a single actuator acting against an opposed spring member. Whatever the mechanism chosen, it is important that the beam angle does not fluctuate as the beam is rotated. It is also desirable to be able to control the exact beam angle.

BRIEF DESCRIPTION OF THE DRAWINGS

Further features of the invention will be better understood by way of the following non-limiting detailed description of a preferred embodiment with reference to the appended drawings, in which.

DETAILED DESCRIPTION OF THE PREFERRED EMBODIMENT

Figure 1:
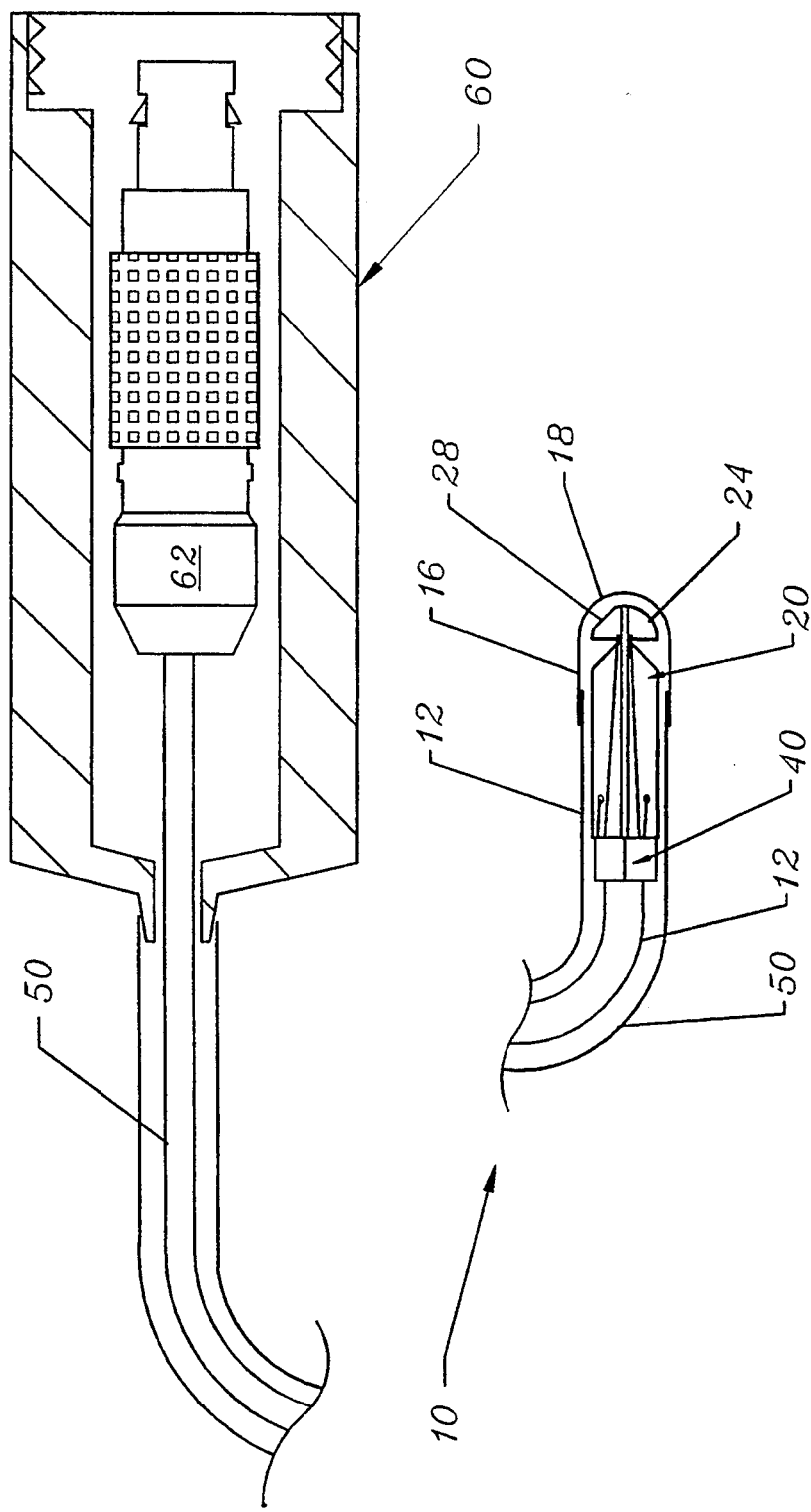
FIG. 1 is a break-away side view of the catheter according to the preferred embodiment.

With reference to FIG. 1, the catheter system (10) according to the preferred embodiment will be described. A thin flexible plastic outer tube (12) has one end connected to a base connector unit (60) and another end connected to a sonolucent chamber capsule (16). A flexible drive shaft (50) is provided in the lumen of tube (12) and is driven by a rotatable member (62) inside connector (60) at the proximal end and is connected to a connector (40) at its distal end. A catheter tip (20) is connected to connector (40) and electrical wires passing through a hollow core in flexible drive shaft (50) connect shape memory alloy wires (30) and transducer (28) to rotatable member (62) which transfers the electrical signals through slip rings to the external circuitry. As rotatable member (62) is rotated, drive shaft (50) is also rotated resulting in rotation of tip (20) inside lumen (14) such that transducer (28) also rotates inside sonolucent chamber capsule (16). Lumen (14) is in practice filled with a sonolucent solution, and a thin marker wire (18) is embedded into the surface of capsule (16) to give a reference marker to transducer (28). The diameter of plastic tube (12) is about 3 mm, however, smaller dimensions are possible and are desirable in order to be able to image blood vessels with a smaller diameter.

Figure 2:
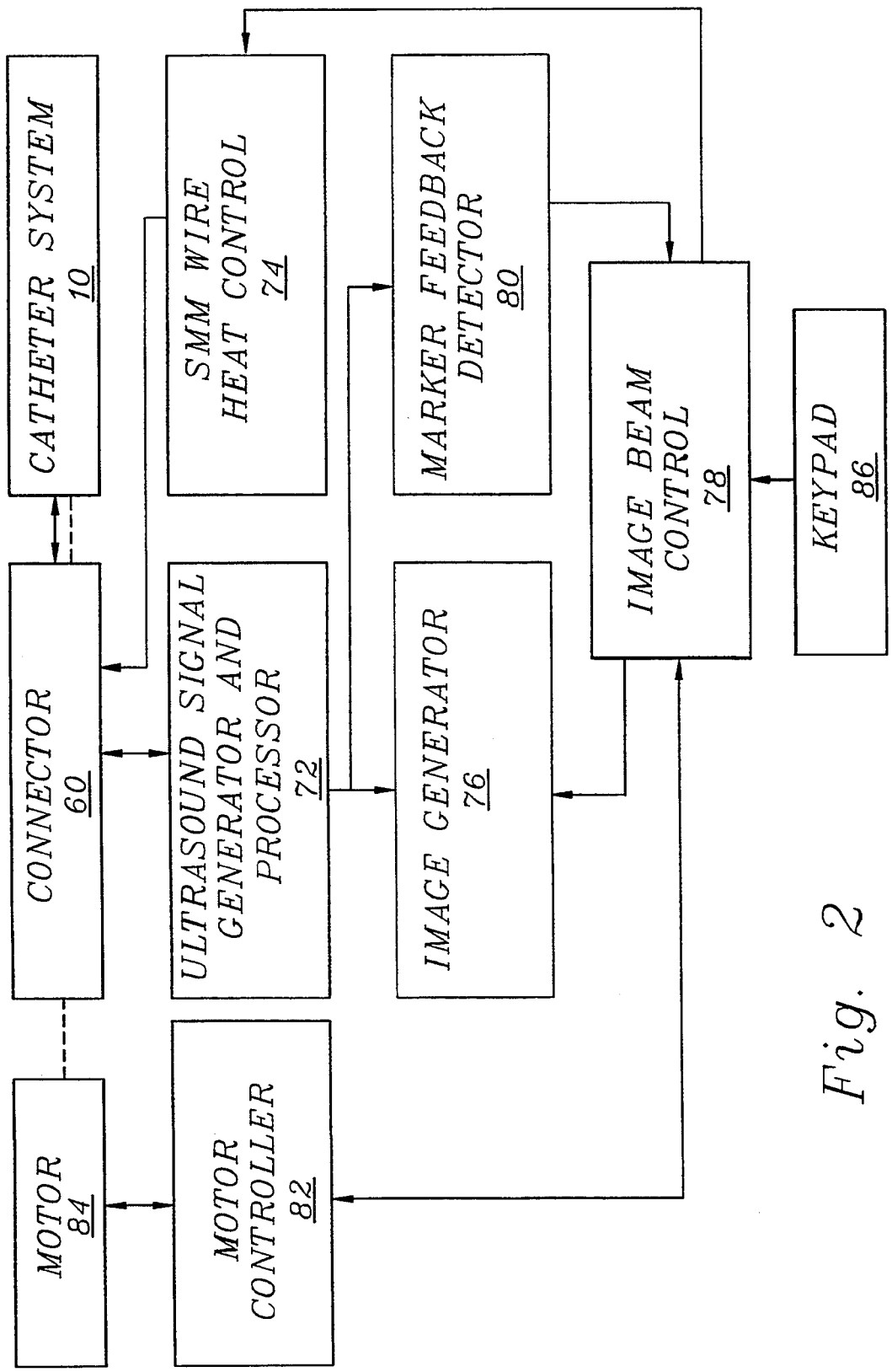
FIG. 2 is a block diagram of the system according to the preferred embodiment.

With reference to FIG. 2, a block diagram of the control system for the catheter system (10) is illustrated. An ultrasound signal generator and processor (72) is connected via rotatable member (62) and a coax (96) provided inside drive shaft (50) to piezoelectric crystal (28). When the crystal is stimulated to produce ultrasonic waves, the echo or reflected waves from the sidewall of the blood vessel or heart chamber stimulates an electric signal in the transducer (28) and produces a return signal which can be processed by the signal processor (72) to provide a measurement of the distance between transducer (28) and the blood vessel sidewall. The amplitude or intensity of the reflected ultrasound beam is indicative of the nature of the material reflecting the beam. For example, a softer material will absorb more and reflect less of the beam than a harder material. Thus, the amplitude of the reflected beam is used to characterize and/or identify the material of the blood vessel sidewall or heart chamber.

An image beam control unit (78) specifies the speed of rotation to motor controller (82) which controls motor (84) to turn drive shaft (50) at a specified rotational speed. A marker feedback detector unit (80) distinguishes detection of marker (18) from detection of the blood vessel sidewall. Based on the distance detected and the duration of the marker echo signal, unit (80) determines the angle of transducer (28) with respect to the axis of rotation. Control unit (78) signals the shape memory alloy wire heating control unit (74) which direction of movement of transducer (28) is desired in order that the control unit (74) may respond by increasing or decreasing current to one of the wires (30). Current from the control unit (74) is fed to wires (30) through connector (62) and conductors contained in drive shaft (50). Unit (74) may comprise a pulse width modulated constant voltage source as is well known in the art. Image beam control unit (78) also informs the image generator as to the transducer angle in order that image generator (76) may display image position data along with the image.

Although a conventional ultrasonograph shows the interior cross-sectional of the blood vessel at a fixed view angle, it is also possible according to the invention to cause transducer (28) to "sweep" through a range of angles, i.e. forward positions, and display a longitudinal section of the blood vessel about a plane co-extensive with the rotational axis of the tip (20). A user input, such as keypad (86) can be used to control the image position, as well as the kind of image, i.e. cross-section, longitudinal section or even a 3-D surface image.

Figure 3:
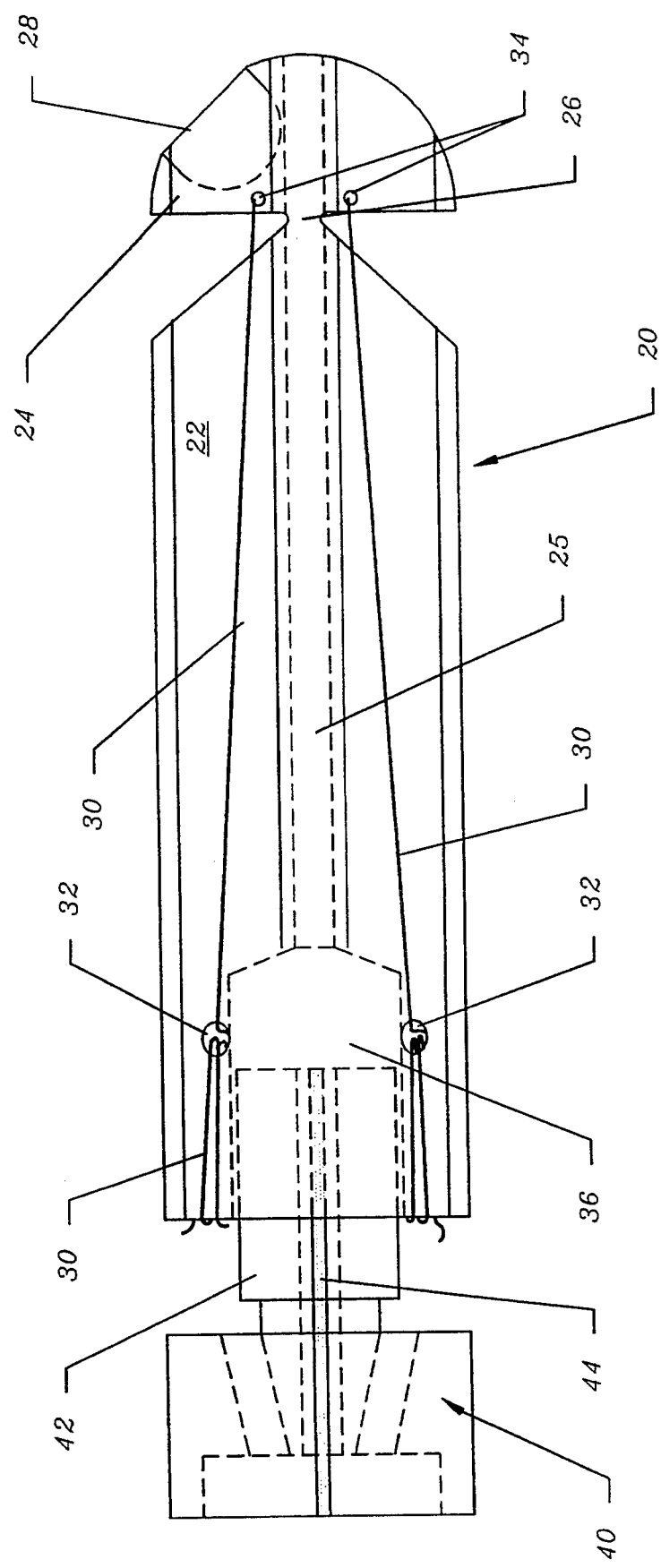
FIG. 3 is a detailed side view of the catheter tip according to the preferred embodiment.
Figure 5:
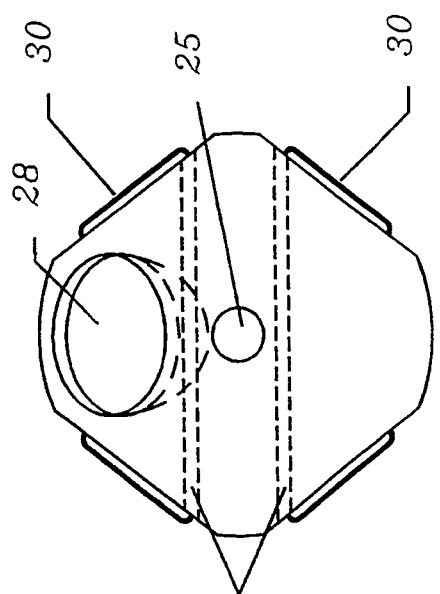
FIG. 5 is a detailed front view of the catheter tip according to the preferred embodiment.
Figure 4:
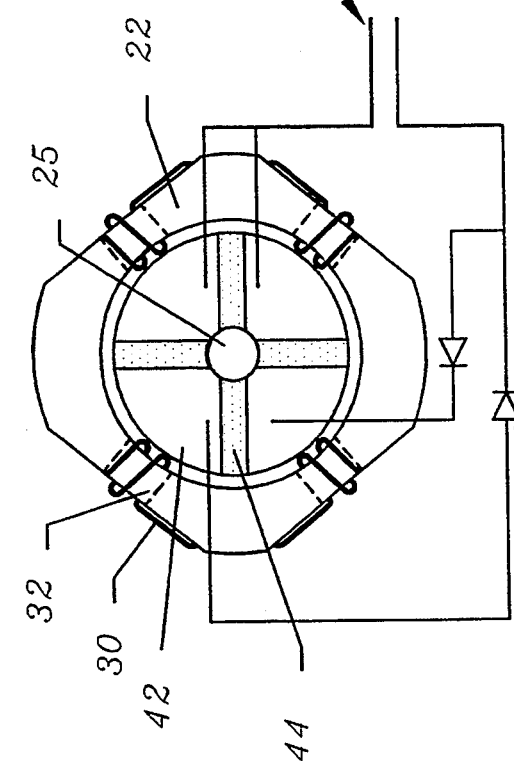
FIG. 4 is a break-away end view of the catheter tip showing the tip connector contacts.
Figure 7:
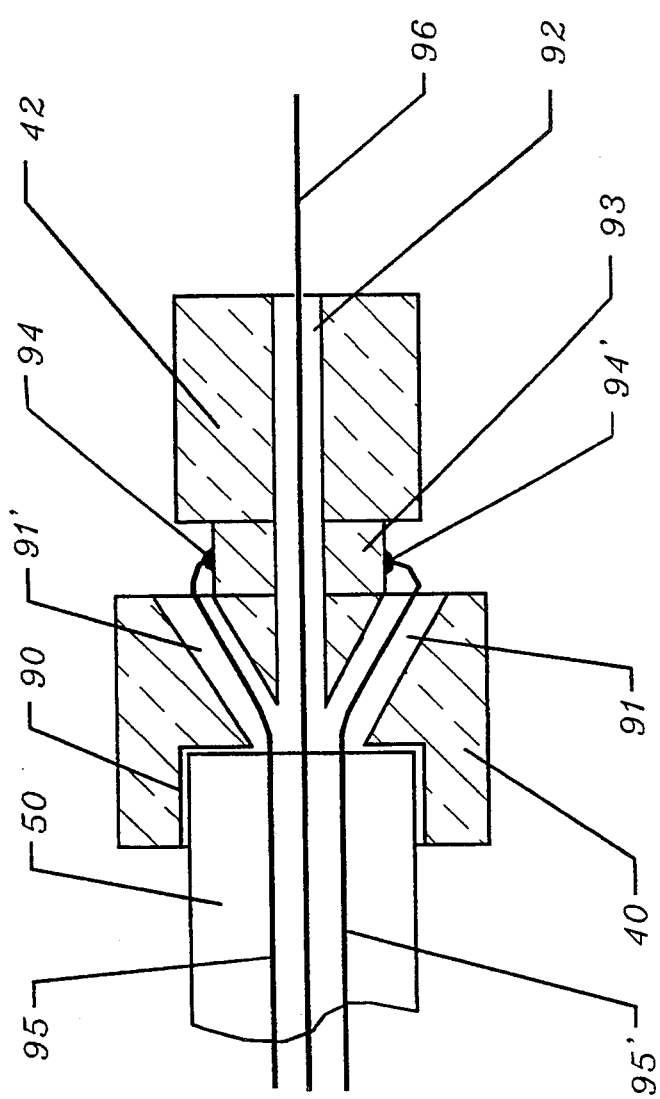
FIG. 7 is a detailed side cut-away view of the tip-to-shaft connector.

As shown in FIG. 3, tip member (20) has a base (22) and a head (24) connected to the base (22) by an integral or living hinge portion (26). Two shape memory material wires (30) extend along the surface of body (22) and through holes (34) as shown in FIGS. 3, 4 and 5. The free ends of wires (30) wrap around the rear edge of body (22) into a socket (36) which receives connector plug (42) of connector (40) and then pass through holes (32). The wires (30) are threaded to loop through socket (36) to keep the wires taut. The connector plug (42) is divided by insulating portions (44) and provides electrical contact between wires (30) and conductors in drive shaft (50). The plug (42) also keeps the wires (30) tightly connected. As detailed in FIG. 7, the plug (42) has a socket (90) for receiving shaft (50), and three channels (91), (91') and (92) for guiding three small coaxial conductors (95), (95') and (96) from shaft (50). Plug (42) and connector (40) comprise four conductive segments connected together by an insulating material. Each conductor (95) and (95') has one wire soldered at neck (93) to opposite "live" segments, while the other two conducting segments are grounded (by the ground wires of conductors (95), not shown). Thus, soldering directly to the shaped memory alloy wires is avoided.

By providing an ohmic heating current source to one of wires (30), a deformation (shrinking) of about 4% to 6% of the length of the wire can be repeatedly created which results in flexing of head (24) in the direction of the heated wire (while the non-heated wire is stretched). When current through the wire is stopped, it returns to ambient temperature within a short time and head (24) returns to its initial position. By balancing current between the two wires (30), head (24) may be pivoted about hinge (26) to flex 45° in either direction resulting in transducer (28) being substantially directed along the axis of rotation of body (22) or perpendicular to the lengthwise axis of rotation. The shape memory material in the preferred embodiment is a nickel-titanium (50:50) alloy wire having a diameter of 75 μm. It is important to operate the wires within their elastic limits. An axial bore (25) shown in FIGS. 3, 4 and 5 provides a passageway for electrical conductor (96) to lead from shaft (50) to transducer (28).

In order to reduce the overall size and number of conductors in drive shaft (50), a pair of diodes (46) may be provided to direct positive current from a single electrical line (48) to one of the wires (30) and negative current to the other wire (30). This arrangement also prevents heating of both wires (30) simultaneously, which may not be desirable.

Figure 6:
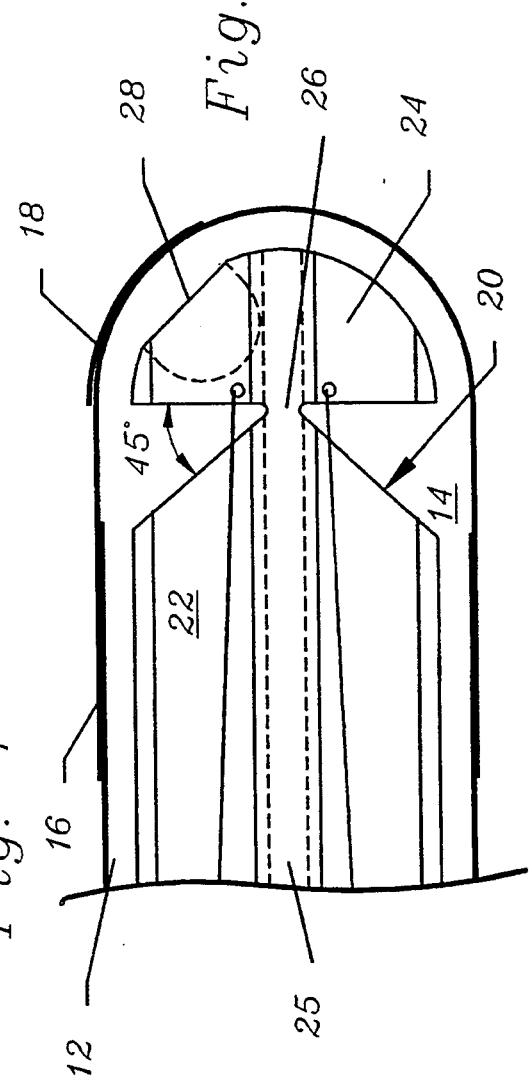
FIG. 6 is a detailed break-away side view of the catheter tip and pivoting head according to the preferred embodiment.

FIG. 6 shows a detailed view of tip (20) inside tube (12) and sonolucent chamber (16). The reference marker strip (18) is a thin wire embedded in an outside of capsule (16) in a plane parallel to the axis of rotation. As described above, marker strip (18) provides a reference signal in order that the beam angle of the ultrasound beam may be determined as well as the zero position of the tip (20) as it is rotated. Head (24) is shown to be somewhat symmetrical in shape, and is able to be flexed 45° in either direction in order to sweep the beam angle of transducer (28) from parallel to the axis of rotation to being perpendicular to the lengthwise axis. The beam angle can be calculated by the distance between the transducer (28) and the wire (18) as well as the fraction of the time the wire echo signal is present with respect to the cycle period, that is the time between consecutive appearances of the wire echo signal.

What is claimed is:
1. An ultrasound catheter comprising:
an outer tube having a lumen, a sonolucent closed distal end and a proximal end;
a flexible rotatable drive shaft provided in said lumen, said shaft including an electric signal transmission cable;
a tip member connected to said shaft and provided at said distal end, said tip member having a length- wise axis of rotation when rotated by said shaft, said tip member having a substantially rigid base and a head pivotally connected to a distal end of said base to pivot about a transverse axis perpendicular to said longitudinal axis;

an ultrasound transducer mounted in said head and connected to said cable for generating an ultrasound beam; and beam directing means for directing said beam radially outward with respect to said lengthwise axis at a variable angle thereto and for controllably adjusting said angle, said beam directing means comprising a thermally deformable conductive member connected between said base and said head for controllably pivoting said head with respect to said base as said member expands and contracts.

2. Catheter as claimed in claim 1, wherein said conductive member comprises a shape memory material wire threaded through a through hole in said head.

3. Catheter as claimed in claim 2, wherein a body of said head and a body of said base are integrally molded from a plastic material interconnected by an integral living hinge.

4. Catheter as claimed in claim 1, wherein two said wires are provided, one connected to each side of said head to pull in said opposite directions about said transverse axis, said wires having free ends connected to said base.

5. Catheter as claimed in claim 4, wherein a body of said head and a body of said base are integrally molded from a plastic material interconnected by an integral living hinge.

6. Catheter as claimed in claim 1, wherein said transducer is mounted in said head at about 45° with respect to said lengthwise axis when said head is in a zero position, said head being displaceable about 45° in either direction from said zero position by said beam directing means, whereby said angle can be adjusted from about 90° to about 0° from said lengthwise axis.

7. Catheter as claimed in claim 6, wherein a body of said head and a body of said base are integrally molded from a plastic material interconnected by an integral living hinge.

8. Catheter as claimed in claim 1, wherein a body of said head and a body of said base are integrally molded from a plastic material interconnected by an integral living hinge.

9. An ultrasound catheter comprising:

an outer tube having a lumen, a sonolucent closed distal end and a proximal end;

a rotatable drive shaft provided in said lumen, said shaft including an electrical signal transmission cable;

a tip member connected to said shaft and provided at said distal end, said tip member having a lengthwise axis of rotation when rotated by said shaft;

an ultrasound transducer mounted in said tip member and connected to said cable for generating an ultrasound beam; and beam directing means for directing said beam radially outward with respect to said lengthwise axis at a variable angle thereto and for controllably adjusting said angle, further comprising an ultrasonically reflective marker strip provided in said sonolucent end, wherein said beam directing means include means to measure a distance between said strip and said transducer and means to determine a value for said angle, said angle being adjusted to be set to a desired value.

10. Catheter as claimed in claim 9, wherein said actuator means comprise a thermally deformable conductive member connected between said base and said head, said deformable member being connected to a variable current source for causing controlled deformation of said deformable member.

11. Catheter as claimed in claim 9, wherein an integral living hinge interconnects said head and said base, and said transducer is mounted in said head at about 45° with respect to said lengthwise axis when said living hinge is in an unflexed position, said head being displaceable about 45° in either direction from said unflexed position, whereby said angle can be adjusted from about 90° to about 0° from said lengthwise axis, said head being displaceable in one direction by ohmic heating of one of said deformable members and said head being displaceable in another direction by ohmic heating of another of said deformable members.

12. An ultrasound catheter comprising:

an outer tube having a lumen, a sonolucent closed distal end and a proximal end;

a rotatable drive shaft provided in said lumen, said shaft including an electrical signal transmission cable;

a tip member connected to said shaft and provided at said distal end, said tip member having a lengthwise axis of rotation when rotated by said shaft;

an ultrasound transducer mounted in said tip member and connected to said cable for generating an ultrasound beam; and beam directing means for directing said beam radially outward with respect to said lengthwise axis at a variable angle thereto and for controllably adjusting said angle, said tip member comprising a base and a head pivotally connected to a distal end of said base to pivot about a transverse axis perpendicular to said longitudinal axis, said transducer being mounted in said head, and said beam directing means including actuator means connected to said base and said head, said actuator means comprising two thermally deformable conductive members connected between said base and said head on opposite sides of said transverse axis, said deformable members being connected to a variable current source for causing controlled deformation of said deformable members, further comprising a diode connected at one end to each one of said deformable conductors, each said diode being connected together at an opposite end and to conduct in a different direction, whereby each said diode can be connected to a single electrical conductor in which when current flows in one direction, only one of said deformable conductors will experience ohmic heating, and when current flows in an opposite direction, only another of said deformable conductors will experience ohmic heating.

13. Catheter as claimed in claim 12, wherein an integral living hinge interconnects said head and said base, and said transducer is mounted in said head at about 45° with respect to said lengthwise axis when said living hinge is in an unflexed position, said head being displaceable about 45° in either direction from said unflexed position, whereby said angle can be adjusted from about 90° to about 0° from said lengthwise axis, said head being displaceable in one direction by ohmic heating of one of said deformable members and said head being displaceable in another direction by ohmic heating of another of said deformable members.

14. An ultrasound catheter comprising:
an outer tube having a lumen, a sonolucent closed distal end and a proximal end;
a rotatable drive shaft provided in said lumen, said shaft including an electrical signal transmission cable;
a tip member connected to said shaft and provided at said distal end, said tip member having a lengthwise axis of rotation when rotated by said shaft;
an ultrasound transducer mounted in said tip member and connected to said cable for generating an ultrasound beam; and
beam directing means for directing said beam radially outward with respect to said lengthwise axis at a variable angle thereto and for controllably adjusting said angle, said beam directing means comprise a shaped memory material wire segment having free ends at a proximal end of said tip member, further comprising press fit means for connecting said wire to conductors coextensive with said shaft, said press fit means including first conductive portions to which said conductors are connected and second conductive portions which said free ends contact by press fit.

15. Catheter as claimed in claim 14, wherein said tip member is non-conductive and provided with a socket at said proximal end of said tip member and a pair of throughholes passing through a side of said tip member into said socket, said free ends extending over said tip member from a distal end thereof into said socket and through said throughholes with one of said free ends passing through only one of said throughholes, said press fit means including a plug member for inserting into said socket, said plug member being connected to said shaft, and including said first conductive portions to which said conductors are connected and said second conductive portions for contacting and securing said free ends.

16. Catheter as claimed in claim 15, wherein said tip member comprises a base and a head pivotally connected to a distal end of said base to pivot about a transverse axis perpendicular to said longitudinal axis, said transducer being mounted in said head, and wherein said catheter comprises two said wire segments each having a middle portion connected to opposite sides of said head to pull said head in opposite directions about said transverse axis.

* * * * *